(12) United States Patent
Lee

(10) Patent No.: US 10,980,449 B2
(45) Date of Patent: Apr. 20, 2021

(54) MINIMALLY INVASIVE CONTINUOUS BLOOD GLUCOSE METER

(71) Applicant: In Han Lee, Edgewood Cliffs, NJ (US)

(72) Inventor: In Han Lee, Edgewood Cliffs, NJ (US)

(73) Assignee: In Han Lee, Edgewood Cliffs, NJ (US)

( * ) Notice: Subject to any disclaimer, the term of this patent is extended or adjusted under 35 U.S.C. 154(b) by 384 days.

(21) Appl. No.: 15/774,505

(22) PCT Filed: Nov. 1, 2016

(86) PCT No.: PCT/KR2016/012463
§ 371 (c)(1),
(2) Date: May 8, 2018

(87) PCT Pub. No.: WO2017/082573
PCT Pub. Date: May 18, 2017

(65) Prior Publication Data
US 2020/0237269 A1    Jul. 30, 2020

(30) Foreign Application Priority Data

Nov. 10, 2015    (KR) ........................ 10-2015-0157574

(51) Int. Cl.
*A61B 5/145* (2006.01)
*A61B 5/00* (2006.01)
*A61B 5/1455* (2006.01)

(52) U.S. Cl.
CPC ........ *A61B 5/14532* (2013.01); *A61B 5/0004* (2013.01); *A61B 5/1455* (2013.01);
(Continued)

(58) Field of Classification Search
CPC ............ A61B 5/14532; A61B 5/14503; A61B 5/6878; A61C 8/00; A61C 8/0012; A61C 8/0022; A61C 8/0024; A61C 8/0025
(Continued)

(56) References Cited

U.S. PATENT DOCUMENTS 5,727,943 A * 3/1998 Beaty ................... A61C 8/0022
                                                                        433/174
2006/0078847 A1* 4/2006 Kwan .................. A61C 8/0001
                                                                        433/174
(Continued)

FOREIGN PATENT DOCUMENTS

JP       2009-039267 A       2/2009
KR   10-2008-0073546 A       8/2008
(Continued)

OTHER PUBLICATIONS

Shafie, Hamid. Implant Abutment Materials. Jul. 25, 2014. John Wiley & Sons, Inc. Chapter 1 Summary. (Year: 2014).*
(Continued)

*Primary Examiner* — Daniel L Cerioni
*Assistant Examiner* — Deirdre M Willgohs
(74) *Attorney, Agent, or Firm* — Christensen, Fonder, Dardi & Herbert PLLC; Diane E. Bennett; Peter S. Dardi

(57) ABSTRACT

According to the present invention, provided is a blood glucose meter comprising: an outer cylinder capable of being coupled within alveolar bone, and having an open lower part; an inner cylinder inserted into and coupled to the inner space of the outer cylinder, and having an open lower part; a biosensor provided in the inner space of the inner cylinder and exposed through the open lower part of the outer cylinder and the open lower part of the inner cylinder; a data processor provided in the inner space of the inner cylinder and receiving a signal from the biosensor and processing the same; a transmitter provided in the inner space of the inner cylinder and transmitting the data of the data processor; and a battery provided in the inner space of the inner cylinder and supplying electric power to the biosensor, the data processor and the transmitter.

7 Claims, 3 Drawing Sheets

(52) U.S. Cl.
CPC ........ *A61B 5/14503* (2013.01); *A61B 5/6878* (2013.01); *A61B 2562/02* (2013.01)

(58) Field of Classification Search
USPC ........................................................ 600/365
See application file for complete search history.

(56) References Cited

U.S. PATENT DOCUMENTS

| | | |
|---|---|---|
| 2013/0197332 A1 | 8/2013 | Lucisano et al. |
| 2015/0177220 A1 | 6/2015 | Lee et al. |

FOREIGN PATENT DOCUMENTS

| | | | | |
|---|---|---|---|---|
| KR | 10-2014-0050787 A | 4/2014 | | |
| KR | 10-2014-0082642 A | 7/2014 | | |
| KR | 101443827 B1 * | 9/2014 | ....... | A61B 5/150015 |
| KR | 101534182 B1 * | 7/2015 | ............. | A61B 5/145 |

OTHER PUBLICATIONS

Schmitt, Christian. Performance of conical abutment (Morse Taper) connection implants: A systematic review. May 9, 2013. Society for Biomaterials. J Biomed Mater Res Part A 2014:102A:552-574. (Year: 2013).*

* cited by examiner

MINIMALLY INVASIVE CONTINUOUS BLOOD GLUCOSE METER

TECHNICAL FIELD

The present application is a National Stage filing of PCT Application No. PCT/KR2016/012463, filed on Nov. 1, 2016, entitled "Minimally Invasive Continuous Blood Glucose Meter," which claims the benefit of priority to Korean Patent Application No. 10-2015-0157574, filed on Nov. 10, 2015, both of which are incorporated herein by reference in their entirety for all purpose.

The present invention relates a blood glucose meter that can continuously measure blood glucose with only minimal invasion, and more specifically, relates to a blood glucose meter implanted in the alveolar bone in the oral cavity for measuring the blood glucose in blood in the microvasculature or interstitial fluid.

BACKGROUND ART

In general, health condition of a human body can be judged by measuring various components contained in blood, and a disease can be estimated and diagnosed if certain components of the blood are out of the normal range. For example, diabetes can be diagnosed by measuring blood glucose contained in blood, or liver disease can be estimated by measuring GOT and GPT.

Recently, diabetes crisis has become a frequent expression of health concerns. For modern people, adult diseases including diabetes are increasing due to dietary changes and lack of exercise, which causes serious problems not only for individuals but also for societies. In particular, diabetes is a disorder in which blood glucose control in the blood is abnormal due to abnormal metabolism. The normal healthy body maintains glucose level in the blood at 72 mg/dL to 144 mg/dL, and blood glucose homeostasis is maintained by insulin hormone secreted from the pancreas regardless of the food taken. However, in diabetic patients, the mechanism of maintaining blood glucose homeostasis is destroyed, and therefore, it is impossible to maintain normal blood glucose, variation range is large, and high blood glucose is maintained in blood, resulting in various complications. Typical complications include angiopathy, retinopathy, neuropathy, and nephropathy, skin complications, coma and the like.

In order to prevent these complications, maintaining the blood glucose homeostasis is the most important. Namely, because the mechanism of automatically maintaining the blood glucose homeostasis in the body is impaired, blood glucose must be maintained artificially. For this purpose, life style of a patient is the most important. Namely, high blood glucose can be lowered and maintained through diet and exercise. On the other hand, pharmacotherapy and hormone (insulin) therapy may be combined. At this time, the important thing is that the patient can frequently monitor himself or herself whether normal blood glucose is maintained or not through repeated blood glucose measurements, and as a result, appropriate lifestyle changes and the pharmacotherapy or hormone therapy can be properly controlled.

In the case of diabetic patients, blood glucose management should be performed through repeated blood glucose measurements. Since the blood glucose meter has been developed for portable use, it is easy for anyone to measure blood glucose, but it is not possible to avoid sticking the skin with a needle for blood sampling. In order to measure blood glucose change accurately, the patient should stick himself or herself with a needle several times a day, and psychological and physical pain caused thereby causes the patient to make accurate blood glucose measurements impossible. For this reason, it is urgently required to develop a device capable of continuous blood glucose measurement with minimal invasion without sticking with a needle.

In order to solve the above problems, a number of implantable measuring devices using biosensors have been developed. The implantable measuring devices are devices that allow a biosensor to detect a specific component from blood flow in the body by implanting a blood measuring device containing a biosensor into the body. Most of the blood measuring devices according to the conventional technology are devices for continuously measuring blood glucose by sticking a biosensor under the skin (subcutaneously) and attaching (by Band-Aid-bio tape and the like) a transmission device to the skin. However, problems of the devices are that the devices are difficult to be fixed because the skin is moving, the sensor is also unavailable for a long period of time (less than about 200 hours), and because the device is not stable, calibration is often needed and there are many inaccurate measurements.

In another type, the blood measuring device has been developed as a type of a tooth implant, and for example, a biosensor placed inside the implant allows blood components such as blood glucose to be measured from blood within the gingival tissue or alveolar bone.

FIG. 1 is a cross-sectional view of a blood measuring device disclosed in Korean Patent No. 1443827.

Referring to the drawing, the blood measuring device of the patent is constructed in the form of a tooth implant. Namely, this blood measuring device comprises a fixture 100 implanted in the patient's bone tissue 10, an abutment 200 joined to the fixture 100, a sensing unit 300 disposed in the abutment 200, a power supplying and transmitting part 500, and a cover 600 joined to the abutment 200. On the cover 600, a dental prosthesis 700 is installed. In the fixture 100, an inner space is formed, and a though-hole 210 to the inner space is formed. A biosensor 320 is disposed for measuring blood flowing through the though-hole 210, and a signal processing component 330 is disposed for processing signal generated in the biosensor 320. Further, the power supplying and transmitting part 500 is connected to the biosensor 320 through a wire 510 for transmitting electric current and signal.

Since the blood measuring device according to the conventional technology is configured with the dental prosthesis 700, there is a problem that stability of the biosensor of the device cannot be secured. Namely, when human chews food, strong pressure is applied to teeth. Thus, the components of the blood measuring device placed below the dental prosthesis 700 are affected by such pressure, and there is a high possibility of breakdown and failure. Moreover, in the blood measuring device, blood should flow through the though-hole 210 to reach the biosensor 320. However, there are problems that the though-hole 210 not only weakens the overall rigidity of the blood measuring device but also makes it impossible to measure blood through the biosensor 320 when blood circulation through the though-hole 210 is not smooth. Further, since the biosensor 320 is placed in the inner space of the abutment 200, there are problems that area of the biosensor 320 necessary for accurate measurement cannot be sufficiently secured, and space for placing the signal processing component 330 is also insufficient.

On the other hand, Korean Patent No. 1534182 discloses a dental implant capable of measuring blood glucose, and the dental implant also have components for measuring blood glucose inside of the dental implant and measures blood glucose in gingival fluid in the oral cavity. However, a problem is that an accurate continuous measurement of blood glucose cannot be made by direct contact with food every time a patient consumes food. Thus, they cannot solve the problems of the conventional technology.

DISCLOSURE

Technical Problem

The present invention has been made in order to solve the above problems of the prior art, and an object of the present invention is to provide a blood glucose meter implanted in the alveolar bone in the oral cavity for measuring blood glucose.

Another object of the present invention is to provide a blood glucose meter with improved structural stability and sufficient room for individual components.

Further, another object of the present invention is to provide a blood glucose meter with accurate measurement and no possibility of infection.

Technical Solution

In order to achieve the above objects, the present invention provides a blood glucose meter comprising:

an outer cylinder, which can be joined in an alveolar bone and has an open bottom;

an inner cylinder having an open bottom, joined to the outer cylinder by being inserted into the inner space of the outer cylinder;

a biosensor disposed in the inner space of the inner cylinder and exposed through the open bottom of the outer cylinder and the open bottom of the inner cylinder;

a data processor disposed in the inner space of the inner cylinder for receiving and processing signal from the biosensor;

a transmitter disposed in the inner space of the inner cylinder for transmitting data from the data processor; and a battery disposed in the inner space of the inner cylinder for supplying power to the biosensor, the data processor and the transmitter.

According to one aspect of the present invention, the outer cylinder further comprises an outer screw formed on a part of the outer surface of the outer cylinder, wherein the outer cylinder is implanted by self-tapping of the outer screw into the alveolar bone.

According to another aspect of the present invention, an inner screw formed on the inner surface of the outer cylinder and the outer screw formed on the outer surface of the inner cylinder are engaged each other.

According to another aspect of the present invention, the inner surface is formed as a tapered surface, for example, morse taper, on top of the outer cylinder, and the outer surface of the inner cylinder is also formed as a corresponding tapered surface such that when the inner cylinder is installed in the outer cylinder, the tapered surface of the outer cylinder and the corresponding tapered surface of the inner cylinder closely contact each other.

According to another aspect of the present invention, the blood glucose meter is implanted in a retromolar pad or an edentulous area and the like in the oral cavity.

According to another aspect of the present invention, the outer cylinder and the inner cylinder are made of a titanium material.

According to another aspect of the present invention, the biosensor senses components contained in the blood flowing through the alveolar bone. The data measured like this can be transmitted to and processed by external devices such as smart phones and wearable devices.

Advantageous Effects

The blood glucose meter according to the present invention is implanted and fixed in a retromolar pad or an edentulous area in the oral cavity, so that it is not affected by the chewing action of teeth, thereby reducing possibility of breakage and failure and improving structural stability. Further, sufficient space for each component for the blood glucose meter can be secured, especially since the biosensor is placed as exposed at the bottom of the blood glucose meter, it can have a sufficient area for measurement. Moreover, the blood glucose meter according to the present invention consists of a double structure of outer and inner cylinders, which allows effective sealing, thereby reducing risk of bacterial infection.

In addition, since the blood glucose meter according to the present invention is fixed in the alveolar bone, the biosensor can stably and continuously measure blood glucose without external interference at the same position. The measured data can be transmitted in real time to a patient's external device such as a smart phone or a wearable device in real time. The patient can be motivated to change his/her life pattern by recognizing the real-time data, and the data becomes a valuable resource for medical staff to establish a treatment plan. When blood glucose changes to dangerous level, for example, a hypoglycemic shock, the medical staff will be automatically contacted so that quick first aid is possible.

BEST MODE CARRYING OUT THE INVENTION

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment does not include every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

Hereinafter, the present invention will be described in more detail with reference to an embodiment shown I the accompanying drawings.

Figure 1:
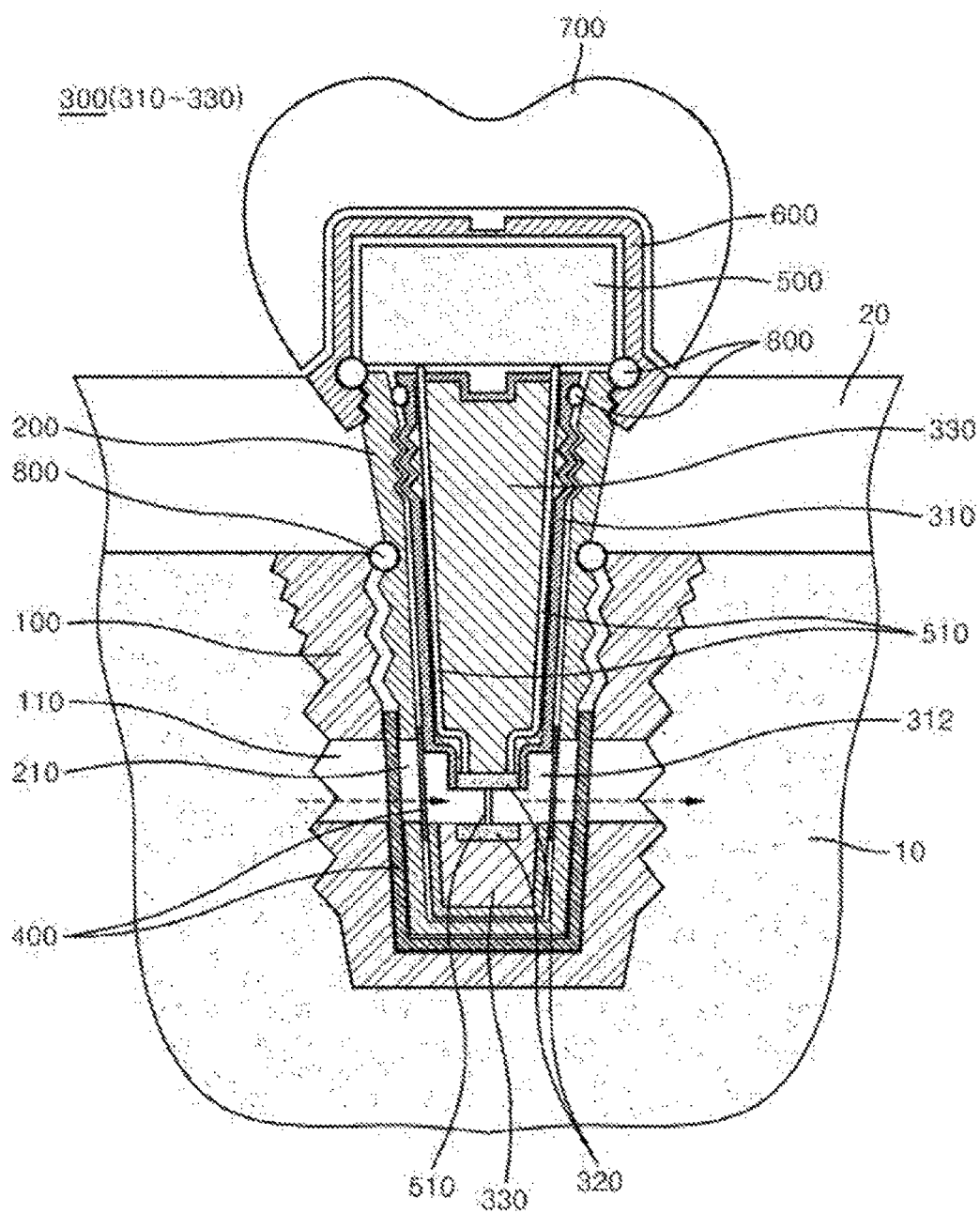
FIG. 1 is a cross-sectional view of a blood glucose meter according to the conventional technology.
Figure 2:
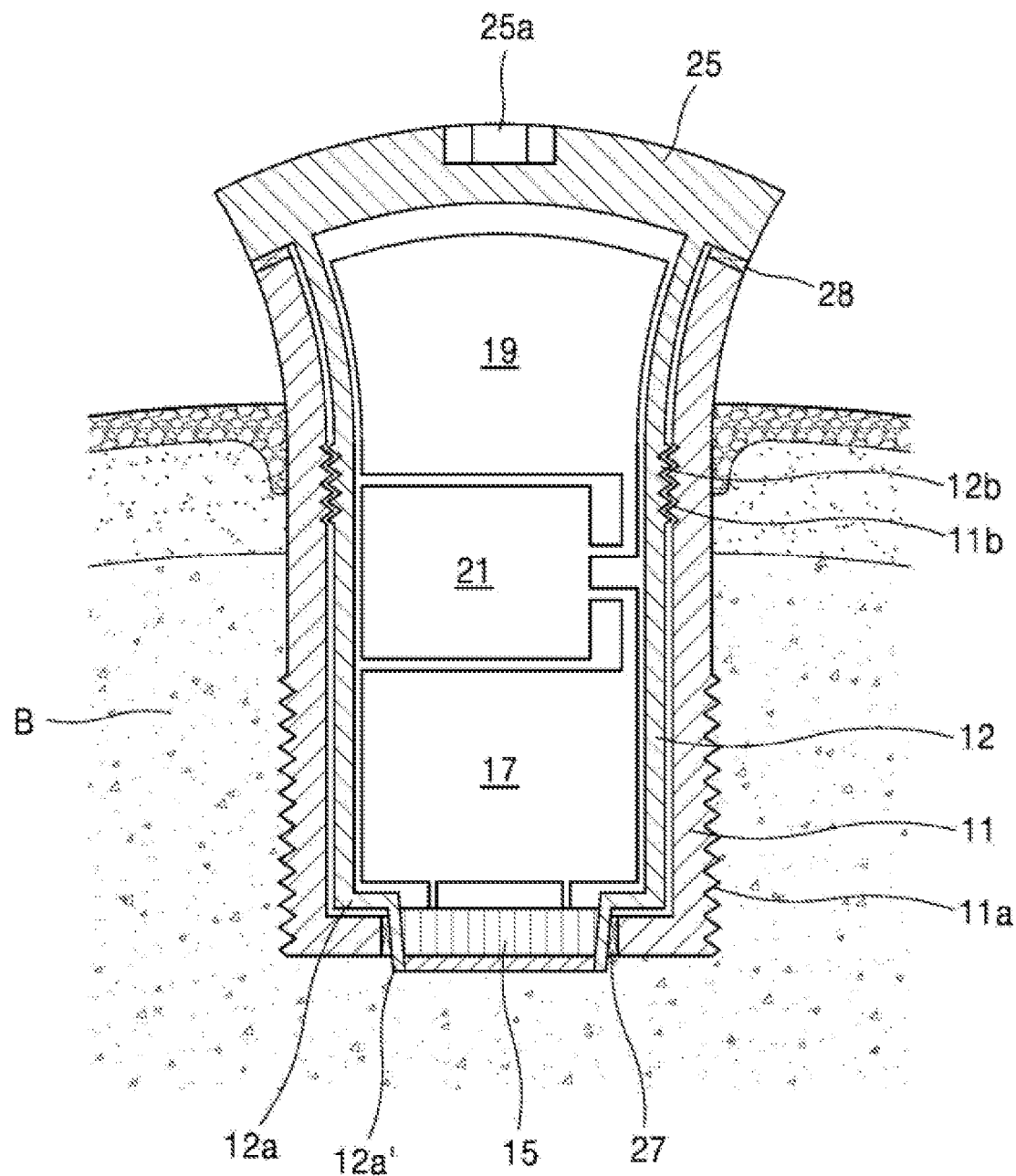
FIG. 2 is a cross-sectional view of a blood glucose meter according to the present invention.

FIG. 2 is a schematic diagram of a blood glucose meter according to an embodiment of the present invention.

Referring to the drawing, the blood glucose meter according to the present invention comprises:

an outer cylinder 11 having an outer screw 11a, which is formed on the outer surface so as to be joined in an alveolar bone B, and an open bottom;

an inner cylinder 12 having an open bottom, joined to the outer cylinder 11 by being inserted into the inner space of the outer cylinder;

a biosensor 15 disposed in the inner space of the inner cylinder 12 and exposed through the open bottom of the outer cylinder 11 and the open bottom of the inner cylinder 12;

a data processor 17 disposed in the inner space of the inner cylinder 12 for receiving and processing signal from the biosensor 15;

a transmitter 19 disposed in the inner space of the inner cylinder 12 for transmitting data from the data processor 17; and a battery 21 disposed in the inner space of the inner cylinder 12 for supplying power to the biosensor 15, the data processor 17 and the transmitter 19.

The outer cylinder 11 has a hollow cylinder shape as a whole and has an outer screw 11a on at least a part of its outer surface. When the blood glucose meter according to the present invention is implanted in a retromolar pad or an edentulous area and the like, the outer cylinder 11 is inserted into the alveolar bone B through the gingival tissue. At this time, the outer screw 11a disposed in the outer cylinder 11 is screwed into the alveolar bone B by being engaged each other while forming a corresponding screw. Namely, the blood glucose meter according to the present invention, disposed in the edentulous area, is relatively less affected by the chewing action of teeth or is not affected at all. The outer cylinder 11 is self-tapped in the alveolar bone B using the outer screw 11a of the outer cylinder 11 so that it can be easily implanted in the oral cavity.

Figure 3:
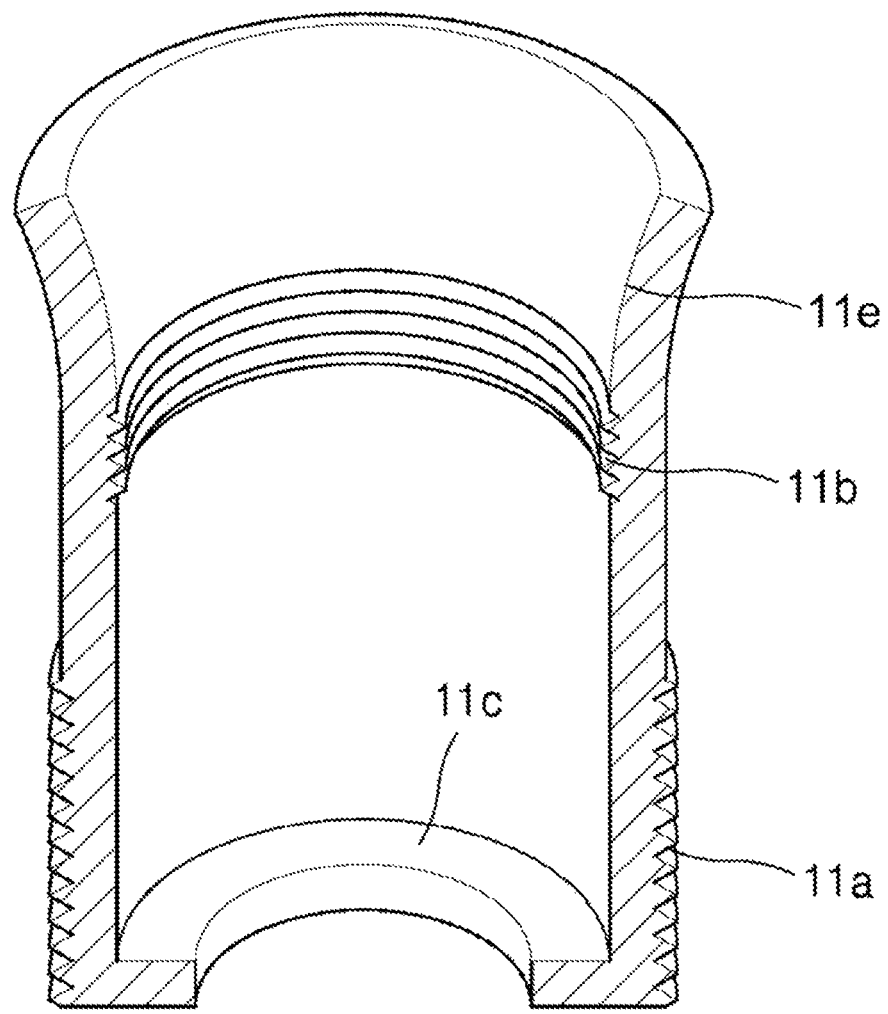
FIG. 3 is a partially cross-sectional perspective view of the outer cylinder of the blood glucose meter illustrated in FIG. 2.

FIG. 3 is a partially cross-sectional perspective view of the outer cylinder.

Referring to the drawing, the top and bottom of the outer cylinder 11 are opened. The biosensor 15 is exposed through the open bottom of the outer cylinder 11. A ring-type seating part 11c is formed at the bottom of the outer cylinder 11. As illustrated in FIG. 2, a stepped part 12a formed at the lower part of the inner cylinder 12 is seated on the ring-type seating part 11c.

The inner cylinder 12 can be inserted through the open top of the outer cylinder 11. An inner screw 11b is formed on at least a part of its inner surface of the outer cylinder 11, and as illustrated in FIG. 2, the inner screw 11b of the outer cylinder 11 is joined to an outer screw 12b formed on at least a part of the outer surface of the inner cylinder 12. It is preferable that the outer cylinder 11 and the inner cylinder 12 are made of a titanium material.

Alternatively or additionally, a polygonal surface may be formed on at least a part of the inner surface of the outer cylinder 11. For example, the polygonal surface may be formed as a hexagonal surface or an octagonal surface. The polygonal surface plays a role of fixing an implant mount (not shown) when implanting the outer cylinder 11 in the alveolar bone. The polygonal surface formed on the inner surface of the outer cylinder 11 may be disposed at a position not overlapped with the inner screw 11b. The distance between the polygonal surfaces facing each other is larger than the diameter of the part where the inner screw 11b is formed. Accordingly, when the inner cylinder 12 is inserted and screwed into the outer cylinder 11, the inner cylinder 12 is not interfered by the polygonal surface.

It is preferable that the inner surface at the top of the outer cylinder 11 is formed as a tapered surface 11e. As illustrated in FIG. 2, it is preferable that the outer surface of the inner cylinder 12 is also formed as a tapered surface so as to correspond to an inner tapered surface 11e of the outer cylinder 11. By forming taper angles of the inner tapered surface 11e of the outer cylinder 11 and the outer tapered surface of the inner cylinder 12 to be different, when the inner cylinder 12 is inserted into the inside of the outer cylinder 11, the tapered surfaces are in contact each other so that its own locking state can be established between the inner cylinder 12 and the outer cylinder 11. Accordingly, unless an external force is applied, it is possible to realize a state in which the inner cylinder 12 inserted into the outer cylinder 11 cannot be separated. Further, the sealing effect between the inner cylinder 12 and the outer cylinder 11 can be expected. Sealing between the inner cylinder 12 and the outer cylinder 11 by the contact between the tapered surfaces can also prevent the bacteria inside the blood glucose meter from infecting the oral cavity. Conversely, it is possible to prevent bacteria by saliva or food in the oral cavity from contaminating the inside of the blood glucose meter.

Referring to FIG. 2 again, a cover 25 is separably or inseparably joined to the open top of the inner cylinder 12. The cover 25 can be joined in various ways, for example, by screwing, welding or adhesion by an adhesive. A tool insertion groove 25a is formed in the center surface of the cover 25. The cover 25 and the inner cylinder 12 joined with the cover 25 can be separated from the outer cylinder 11 by inserting a tool (not shown) into the tool insertion groove 25a and rotating it.

A protrusion 12a' may be formed in the lower part of the inner cylinder 12 together with the stepped part 12a. The protrusion 12a' may protrude through the open bottom of the outer cylinder 11, or the bottom plane of the protrusion 12a' and the bottom plane of the outer cylinder 11 may be coplanar. The biosensor 15 is disposed inside the protrusion 12a'. It is preferable that a sealing member 27 may be disposed between the protrusion 12a' and the corresponding surface of the outer cylinder 11.

It is preferable that the outer edge of the cover 25 is extended to be formed as a flange covering the upper end of the outer cylinder 11. When the cover 25 is joined with the upper end of the inner cylinder 12, the edge of the cover 25 contacts the upper end of the outer cylinder 11. The inner space of the outer cylinder 11 can be sealed by disposing the sealing member 28 between the upper end of the outer cylinder 11 and the edge of the cover 25.

The biosensor 15 is disposed in the protrusion 12a' at the lowest part of the inner cylinder 12 and exposed through the open bottom of the inner cylinder 12 and the open bottom of the outer cylinder 11. As a result, the biosensor 15 can be kept in constant contact with blood stream flowing through the alveolar bone B, and thus can detect blood components. The biosensor 15 may be any type of sensor known in the art, for example, an optical biosensor, an electrochemical biosensor and the like.

MODE FOR INVENTION

The present invention will be explained in detail with reference to the following examples, including test examples. However, these examples are provided for illustrative purposes only and are not intended to limit the scope of the invention.

In another embodiment not shown in the drawings, the biosensor 15 may be disposed inward from the bottom surface of an outer cylinder 11. Namely, the protrusion 12a' of the inner cylinder 12 is not protruded beyond the bottom of the outer cylinder 11 so that the biosensor 15 is displaced so that a space is formed between the bottom surface of the biosensor 15 and the bottom surface of the outer cylinder 11.

A data processor 17 is disposed on top of the biosensor 15. The data processor 17 processes the data including the optical, chemical or electrical data of blood stream sensed by the biosensor 15 and then converts it into electrical signal. The data processor 17 communicates with a transmitter 19 so that the data of blood stream can be transmitted to the outside as electrical signal via the transmitter 19. The signal transmitted from the transmitter 19 may be received and displayed on, for example, a smart phone.

A battery 21 is disposed in the inner space of the inner cylinder 12 to supply power to the biosensor 15, the data processor 17 and the transmitter 19. In the example shown in the drawing, the battery 21 is disposed between the transmitter 19 and the data processor 17, but it is also possible to arrange them differently. For example, the battery 21 may be disposed at the uppermost position, or positions of the battery 21 and the data processor 17 may be exchanged with each other.

The blood glucose meter according to the present invention can be used particularly for measuring blood glucose. The blood glucose meter according to the present invention can be installed by inserting the outer cylinder 11 into the alveolar bone B by self-tapping with the outer screw 11a and then inserting the inner cylinder 11 into the outer cylinder 11. At this time, the inner cylinder 12 contains all the components including the biosensor 15, and the open upper end of the inner cylinder 12 is closed by the cover 25.

The inner cylinder 12 can be inserted and installed in the outer cylinder 11 through engagement between the screws 11b, 12b. At this time, a tool insertion groove 25a formed in the cover 25 can be used to rotate the inner cylinder 12. When the inner cylinder 12 is completely installed inside the outer cylinder 11, the biosensor 15 can be exposed to blood stream of the alveolar bone B through the bottom of the outer cylinder 11. On the other hand, when the battery 21 is consumed and its replacement is necessary, or when normal blood measurement operation is not performed, only the inner cylinder 12 can be removed while the outer cylinder 11 left is placed inside the alveolar bone B. The biosensor 15 is provided in a completely bonded state to the inner cylinder 12, and a biocompatible adhesive is used between the biosensor 15 and the inner cylinder 12 to enable sealing of the inner cylinder.

INDUSTRIAL AVAILABILITY

In the blood glucose meter according to the present invention fixed in the alveolar bone, the biosensor can stably and continuously measure blood glucose without external interference at the same position. The measured data can be transmitted in real time to a patient's external device such as a smart phone or a wearable device in real time. The patient can be motivated to change his/her life pattern by recognizing the real-time data, and the data becomes a valuable resource for medical staff to establish a treatment plan. When blood glucose changes to dangerous level, for example, a hypoglycemic shock, the medical staff will be automatically contacted so that quick first aid is possible.

Although specific embodiments of the present invention are described in detail as described above, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A blood glucose meter comprising:
an outer cylinder, which can be joined in an alveolar bone and has an open bottom;
an inner cylinder having an open bottom, joined to the outer cylinder by being inserted into the inner space of the outer cylinder;
a biosensor disposed in the inner space of the inner cylinder and exposed through the open bottom of the outer cylinder and the open bottom of the inner cylinder;
a data processor disposed in the inner space of the inner cylinder for receiving and processing a signal from the biosensor;
a transmitter disposed in the inner space of the inner cylinder for transmitting data from the data processor; and
a battery disposed in the inner space of the inner cylinder for supplying power to the biosensor, the data processor and the transmitter,
wherein the inner cylinder comprises a protrusion at the lowest part of the inner cylinder with the open bottom of the inner cylinder corresponding to an open edge of the protrusion and the inner space of the protrusion being a portion of the inner space of the inner cylinder,
wherein the protrusion protrudes through the open bottom of the outer cylinder, or the bottom plane of the protrusion and the bottom plane of the outer cylinder is coplanar,
wherein the biosensor is disposed in the protrusion.

2. The blood glucose meter according to claim 1, wherein the outer cylinder further comprises an outer screw formed on a part of the outer surface of the outer cylinder, wherein the outer cylinder is implanted by self-tapping of the outer screw into the alveolar bone.

3. The blood glucose meter according to claim 1, wherein an inner screw formed on the inner surface of the outer cylinder and an outer screw formed on the outer surface of the inner cylinder are engaged with each other.

4. The blood glucose meter according to claim 1, wherein the inner surface of the outer cylinder is formed as a tapered surface on top of the outer cylinder, and the outer surface of the inner cylinder is also formed as a corresponding tapered surface such that when the inner cylinder is installed in the outer cylinder, the tapered surface of the outer cylinder and the corresponding tapered surface of the inner cylinder contact each other.

5. The blood glucose meter according to claim 1, wherein the outer cylinder and the inner cylinder are made of a titanium material.

6. The blood glucose meter according to claim 1, wherein the biosensor senses components contained in the blood flowing through the alveolar bone.

7. A method of placing a blood glucose meter, the method comprising implanting the blood glucose meter of claim 1 in a retromolar pad or an edentulous area in the oral cavity.

* * * * *